US011865318B2

(12) United States Patent
Jugl et al.

(10) Patent No.: US 11,865,318 B2
(45) Date of Patent: Jan. 9, 2024

(54) INJECTION DEVICE WITH DOSE SIZE ADJUSTER

(71) Applicant: SANOFI, Paris (FR)

(72) Inventors: Michael Jugl, Frankfurt am Main (DE); Stefan Blancke, Frankfurt am Main (DE)

(73) Assignee: Sanofi, Paris (FR)

( * ) Notice: Subject to any disclaimer, the term of this patent is extended or adjusted under 35 U.S.C. 154(b) by 595 days.

(21) Appl. No.: 16/976,963

(22) PCT Filed: Feb. 27, 2019

(86) PCT No.: PCT/EP2019/054813
§ 371 (c)(1),
(2) Date: Aug. 31, 2020

(87) PCT Pub. No.: WO2019/166469
PCT Pub. Date: Sep. 6, 2019

(65) Prior Publication Data
US 2021/0369975 A1 Dec. 2, 2021

(30) Foreign Application Priority Data

Mar. 1, 2018 (EP) ..................................... 18305215

(51) Int. Cl.
*A61M 5/315* (2006.01)
*A61M 5/24* (2006.01)

(52) U.S. Cl.
CPC .... *A61M 5/31585* (2013.01); *A61M 5/31515* (2013.01); *A61M 5/31526* (2013.01);
(Continued)

(58) Field of Classification Search
CPC .......... A61M 5/31585; A61M 5/31515; A61M 5/32; A61M 5/31526; A61M 5/31595; A61M 2005/2477; A61M 2005/31516
See application file for complete search history.

(56) References Cited

U.S. PATENT DOCUMENTS 3,884,230 A    5/1975  Wulff
9,205,199 B2 * 12/2015  Kemp ................. A61M 5/2033
(Continued)

FOREIGN PATENT DOCUMENTS

JP    2007-509726    4/2007
JP    2013-506453    2/2013
JP    2016-528000    9/2016

OTHER PUBLICATIONS

PCT International Preliminary Report on Patentability in International Appln. No. PCT/EP2019/054813, dated Sep. 1, 2020, 8 pages.
(Continued)

*Primary Examiner* — Dung T Ulsh
(74) *Attorney, Agent, or Firm* — Fish & Richardson P.C.

(57) ABSTRACT

The present disclosure relates to an injection device configured to expel a dose of a medicament, the injection device comprising: an elongated housing extending in a longitudinal direction, a piston rod movable relative to the housing in a longitudinal distal direction to exert a dispensing pressure onto a bung of a cartridge at least partially filled with an injectable medicament, a rod extension movably arranged on or in a distal end of the piston rod, a driver operably engaged with the piston rod and movable relative to the housing in a longitudinal proximal direction for setting of the dose and movable relative to the housing in the longitudinal distal direction for dispensing of the dose, and an adjuster arranged on or in the driver and operably engaged with the rod extension to move the rod extension in longitudinal direction relative to the piston rod.

21 Claims, 4 Drawing Sheets

(52) U.S. Cl.
CPC . *A61M 5/31595* (2013.01); *A61M 2005/2477* (2013.01); *A61M 2005/31516* (2013.01)

(56) References Cited

U.S. PATENT DOCUMENTS

| | | |
|---|---|---|
| 9,750,890 B2 | 9/2017 | Kouyoumjian et al. |
| 10,420,890 B2 | 9/2019 | Jugl et al. |
| 2006/0270985 A1 | 11/2006 | Hommann et al. |
| 2007/0017533 A1 | 1/2007 | Wyrick |
| 2013/0006192 A1 | 1/2013 | Teucher et al. |
| 2015/0112274 A1* | 4/2015 | Quinn ............... A61M 5/31585 604/207 |
| 2017/0319789 A1* | 11/2017 | Veasey ............... A61M 5/31593 |
| 2018/0140776 A1* | 5/2018 | Bengtsson ........ A61M 5/31581 |

OTHER PUBLICATIONS

PCT International Search Report and Written Opinion in International Appln. No. PCT/EP2019/054813, dated Mar. 29, 2019, 11 pages.

\* cited by examiner

INJECTION DEVICE WITH DOSE SIZE ADJUSTER

CROSS-REFERENCE TO RELATED APPLICATIONS

The present application is the national stage entry of International Patent Application No. PCT/EP2019/054813, filed on Feb. 27, 2019, and claims priority to Application No. EP 18305215.8, filed on Mar. 1, 2018, the disclosures of which are incorporated herein by reference.

TECHNICAL FIELD

The present disclosure relates in one aspect to an injection device, such as a pen-type injector for setting and dispensing of a dose of a medicament. In particular, the disclosure relates to a so-called fixed dose injection device configured to set and to expel a dose of a medicament of a fixed, hence non-variable size.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, the dose setting as well as dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a longitudinally movable piston rod which is configured to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast, injection devices of disposable type are to be discarded when the medicament in the cartridge has been dispensed or used-up.

For some applications it is sufficient, when the injection device is configured to set and to expel doses of equal size. Such injection devices are typically denoted as fixed dose devices. They offer repeated setting and expelling of a single predefined dose of the medicament. General handling and operation of such fixed dose injection devices is rather simple and straightforward. Such fixed dose injection devices may be configured and provided as disposable injection devices. They are intended to be discarded when the medicament disposed therein has been used up.

SUMMARY

For some application scenarios it is desirable to vary the size of a predefined fixed dose within predefined margins. It is hence desirable to provide a temporary or a preliminary reduction or increase of a fixed dose. It may be desirable to provide an at least one-time modification of a fixed dose. In this way the patient himself may decide to reduce or to increase a fixed size of a dose to avoid any eventual discomfort or intolerance with regard to the medicament. For some patients administering of a fixed predefined dose of a medicament may lead to sickness at least under particular circumstances, e.g. in the morning or in the beginning of a therapy. For such particular circumstances it is desirable to provide an injection device that offers setting and expelling of a dose that slightly differs from the fixed predefined dose.

It is hence desirable to provide a fixed dose injection device with a dose size adjuster.

In one aspect there is provided an injection device that is configured to expel a dose of a medicament. The injection device comprises an elongated housing extending in a longitudinal direction. The injection device further comprises a piston rod movable relative to the housing in a longitudinal distal direction to exert a dispensing pressure onto a bung or piston of a cartridge. The cartridge is at least partially filled with an injectable medicament. The injection device further comprises a rod extension that is movably arranged on or in a distal end of the piston rod. The injection device further comprises a driver operably engaged with the piston rod and movable relative to the housing in a longitudinal proximal direction for setting of the dose. The driver is further movable relative to the housing in the longitudinal distal direction for dispensing of the dose. The injection device further comprises an adjuster that is arranged on or in the driver. The adjuster is operably engaged with the rod extension to move the rod extension in longitudinal direction relative to the piston rod.

The adjuster is user operable and enables an individual longitudinal displacement of the rod extension relative to the piston rod. The adjuster is configured to vary the length of a rod assembly. The rod assembly may be constituted by the piston rod and the rod extension connected to the piston rod. The rod assembly is of variable length. The longitudinal extension of the rod assembly, hence the length of the rod assembly depends on the longitudinal or axial position of the rod extension relative to the piston rod. By reducing the length of the rod assembly, e.g. by displacing the rod extension in proximal direction relative to the piston rod the size of a dose to be expelled by the injection device can be reduced. By increasing the length of the rod assembly, e.g. by displacing the rod extension in distal direction relative to the piston rod the size of a dose to be expelled by the injection device can be increased.

The rod assembly may further comprise a pressure piece arranged at a distal end of the rod extension. The distal end of the rod assembly or the pressure piece may be in direct axial or longitudinal abutment with a proximal face of the bung of the cartridge. The adjuster is typically operable before, during or after setting of a dose. Setting of a dose may be conducted by retracting the driver or a button connected to the driver in proximal direction relative to the housing. Operation of the adjuster leads to a shortening or to an extension of the rod assembly.

Typically, the adjuster is actuatable, i.e. movable or rotatable in a first direction for increasing a size of a dose. The adjuster is actuatable, i.e. movable or rotatable also in a second direction opposite to the first direction for decreasing of the size of the dose. Operating the adjuster in the first direction leads to a distally directed displacement of the rod extension relative to the piston rod. Operating the adjuster in the second direction leads to a proximally directed displacement of the rod extension relative to the piston rod. Moving or rotating the adjuster in the first direction leads to a length reduction of the rod assembly. Moving or rotating the adjuster in the second direction leads to an increase of the length of the rod assembly. Both operations of the adjuster, hence a dose increasing as well as a dose decreasing operation of the adjuster may be conducted while or as the distal end of the rod assembly is in direct contact with the bung of the cartridge.

Moving the adjuster in the second direction leads to a retraction of the rod extension in proximal direction. Then, the rod extension may lose contact with the proximal face of the bung of the cartridge. Moving the adjuster in the first direction leads to an increase of the longitudinal extension of the rod assembly and hence to a distally directed displacement of the rod extension relative to the piston rod. Typically, the total displacement of the rod extension relative to the piston rod that is inducible by the adjuster leads to a pretension or pre-stressing of the expelling mechanism or drive mechanism of the injection device without displacing the bung in distal direction. Hence, the adjuster-inducible distally directed displacement of the rod extension relative to the piston rod is smaller than or equal to a longitudinal breakaway displacement of the rod assembly that is required to overcome a breakaway force of the piston relative to the barrel of the cartridge.

The driver is either directly or indirectly user accessible. The driver is at least operably engageable with the piston rod when displaced in distal direction relative to the housing. The driver is or may be operably disconnected from the piston rod when displaced in proximal direction relative to the housing. The driver may be in a sliding longitudinal engagement with the housing.

In one example the driver is rotationally locked to the housing. Typically, the driver is movable back-and-forth in longitudinal direction relative to the housing. The driver may be in a splined engagement with the housing. The driver is hindered to rotate relative to the housing but is free to slide along the longitudinal direction of the housing.

In a further example the driver is threadedly engaged with the piston rod. In this way, a longitudinal displacement of the driver relative to the housing may lead to a rotation of the piston rod relative to the housing. A longitudinal displacement of the driver induces a torque onto the piston rod. Typically, a distally directed displacement of the driver relative to the housing may induce a driving torque to the piston rod. Moreover, the piston rod may be threadedly engaged with the housing. A longitudinal displacement of the driver relative to the housing may be induced through a screw motion of the piston rod relative to the housing. Due to the threaded engagement between the piston rod and the housing the piston rod experiences a distally directed displacement relative to the housing as the driver is displaced in distal direction relative to the housing.

Depending on the lead of the threaded engagement of the piston rod with the driver and depending on the lead of the threaded engagement of the piston rod with the housing a reduction ratio between the distally directed motion of the driver and a distally directed motion of the piston rod relative to the housing can be provided. Typically, the piston rod comprises a first threaded section in threaded engagement with the housing and the piston rod further comprises a second threaded section in threaded engagement with the driver. The ratio of the lead of the first threaded section and the lead of the second surface section defines the reduction ratio. The first threaded section and the second threaded section may be of opposite hand.

According to another example the piston rod comprises at least one flexible guide feature that is threadedly engaged with a screw thread of the driver. The flexible guide feature may be provided at a proximal end of the piston rod. It may be located inside a hollow section of the driver. The screw thread of the driver threadedly engaged with the flexible guide feature may be provided at an inside wall of the driver. The flexible guide feature is radially deflectable. It is radially inwardly deflectable as the driver is displaced in proximal direction relative to the housing. During such a proximally directed displacement of the driver the piston rod may be hindered to rotate.

The flexible guide feature may be deflected inwardly so as to temporally disengage from the screw thread of the driver. This enables a proximally or longitudinally directed displacement of the driver relative to the housing while the piston rod remains rotationally fixed to the housing. As the driver reaches a predefined cocked state relative to the housing the flexible guide feature of the piston rod re-engages with a proceeding screw thread of the driver. In other words, the flexible guide feature enables a proximally directed displacement of the driver relative to the piston rod and hence a temporary disengagement of the driver and the piston rod. The flexible guide feature is further configured to transfer a distally directed displacement of the driver relative to the housing into a rotational motion of the piston rod relative to the housing during and for dispensing of a dose.

According to a further example the adjuster is axially engaged with the driver. The adjuster is axially connected with the driver. In other words, the adjuster moves back and forth in proximal and in distal direction relative to the housing as the driver is displaced proximally from an idle state into a cocked state and as the driver returns from the proximal cocked state into the distalmost idle or initial state. Since the adjuster is axially engaged with the driver it is and remains user accessible. This enables an individual dose size adjustment whenever required.

According to a further example the adjuster is in a longitudinal sliding engagement with the rod extension. In this way, the adjuster is able to slide in axial direction relative to the rod extension as the driver is subject to a longitudinally directed displacement relative to the housing. During a proximally directed displacement of the driver relative to the housing the rod extension is and remains fixed relative to the housing and to the piston rod. During a distally directed displacement of the driver relative to the housing the rod extension is configured to rotate and to move together with the piston rod.

The longitudinal sliding engagement between the adjuster and the rod extension enables a rather flexible and universal manipulation or actuation of the rod extension. In any axial position of the driver, the adjuster is and remains in sliding engagement with the rod extension. Hence, in any longitudinal position of the adjuster and/or of the driver the longitudinal position of the rod extension relative to the piston rod can be manipulated by the adjuster.

According to a further example the adjuster is rotationally locked to the rod extension. In this way, a rotation of the adjuster is transferable into a respective rotation of the rod extension. Typically, the adjuster is in splined engagement with the rod extension. The splined engagement is configured to transfer an angular momentum or a torque between the adjuster and the rod extension. A rotation of the adjuster relative to the piston rod is hence transferable into a rotation of the rod extension relative to the piston rod.

In a further example the rod extension is threadedly engaged with the distal end of the piston rod. In this way, a rotation of the rod extension relative to the piston rod leads to a longitudinal displacement of the rod extension relative to the piston rod. By rotating the rod extension relative to the piston rod the overall longitudinal size of the rod assembly can be varied.

Typically, the piston rod is hollow. It may comprise a hollow cavity. The cavity may be open towards a proximal end and/or towards a distal end. The adjuster comprises a threaded section configured as an outer thread which is threadedly engaged with a correspondingly shaped inner thread on an inside section of the hollow piston rod. The rod extension further comprises a rod section provided with at least one spline feature in splined engagement with a corresponding spline feature of the adjuster. The mutually corresponding spline features of the rod extension and the adjuster comprise at least one radial protrusion located in a correspondingly or complementary shaped radial recess.

The rod extension is typically located inside the cavity of the piston rod. The adjuster is typically located inside the cavity of the piston rod. One of the rod extension and the adjuster comprises a hollow cavity to receive the other one of the rod extension and the adjuster; or vice versa. In this way, an axially and radially overlapping arrangement of the rod extension and the adjuster can be provided thus enabling a permanent torque proof engagement thereof and allowing for an axial longitudinal displacement relative to each other.

For instance, at least one of the rod extension and the adjuster comprises a radial protrusion located in a correspondingly or complementary shaped radial recess of the other one of the rod extension and the adjuster. At least one of the mutually corresponding spline features of the adjuster and the rod extension comprises a longitudinal extension that is at least equal to or larger than a longitudinal displacement path of the driver between the initial or idle state and the cocked state. In this way the rod extension and the adjuster remain in splined engagement even if the adjuster is subject to a longitudinal displacement as the driver is moved in longitudinal direction for setting and/or for dispensing of a dose.

Typically, the spline feature of the rod extension is provided at a proximal end of the rod extension whereas the threaded section is located at a distal end of the rod extension. The cross-section of the rod section may comprise a smaller diameter than the threaded section of the rod extension. The difference in diameter of the threaded section and the rod section may correspond to the radial thickness of a distal section of the adjuster. In this way at least the distal section of the adjuster can be arranged radially overlapping with the rod section inside the hollow piston rod. Both, the rod extension and the adjuster can be axially or longitudinally guided by and inside the hollow piston rod. The piston rod itself may be longitudinally or axially guided by an inner thread or by a threaded insert located inside the housing of the injection device.

According to a further example the adjuster is rotatable relative to the piston rod when an adjusting torque above a predefined holding torque is applied to the adjuster. The holding torque is larger than a driving torque required for displacing the piston rod in distal direction during dispensing of the dose. During an adjustment operation, e.g. before, during or after setting of a dose and while the driver is at least temporally axially fixed relative to the housing also the piston rod remains rotationally locked to the housing due to the threaded engagement between the piston rod and the driver. Then, an adjusting torque can be applied to the adjuster either in the first direction or in the second direction. Typically, the adjuster can be rotated clockwise or counterclockwise relative to the driver or relative to the housing for adjusting the fixed dose in an increasing or decreasing manner, respectively.

For the purpose of dose dispensing and under normal operating conditions a driving torque applied to the piston rod typically does not exceed the holding torque. The rotational interlock between the piston rod and the rod extension is torque limited by the predefined holding torque. This prevents a rotation of the rod extension relative to the piston rod during a dose dispensing or dose expelling procedure. For adjusting of the size of the fixed dose a torque above the predefined holding torque has to be applied to the adjuster in order to overcome the rotational interlock between the piston rod and the rod extension.

According to a further example there is provided at least one of a frictional engagement and a ratchet engagement between the adjuster and the piston rod. The mutual mechanical engagement between the adjuster and the piston rod defines the predefined holding torque. The adjuster is in permanent rotational interlock with the rod extension and the rod extension is in threaded engagement with the piston rod. For modifying the overall axial extension of the rod assembly the adjuster has to be rotated relative to the piston rod. Through the at least one of a ratchet engagement and a frictional engagement between the adjuster and the piston rod a self-acting or an automatic length adjustment of the rod assembly can be effectively prevented.

Due to the at least one of the ratchet engagement and the frictional engagement between the adjuster and the piston rod the total length of the rod assembly can be fixed. The total length of the rod assembly can only be modified as an adjusting torque larger than the holding torque is applied to the adjuster relative to the piston rod. This provides an additional safety feature to prevent an unintentional modification of the predefined and fixed size of the dose.

According to a further example there is provided an intermediate piece arranged between the rod extension and the adjuster. The intermediate piece is rotationally locked to the rod extension and to the adjuster. The intermediate piece allows and supports a longitudinal displacement of the adjuster relative to the rod extension. The intermediate piece may further provide a dedicated frictional engagement and/or ratchet engagement with the piston rod.

The intermediate piece may be in splined engagement with at least one of the adjuster and the rod extension. The intermediate piece may be in splined engagement with both, namely with the rod extension and with the adjuster.

According to a further example the intermediate piece is in sliding engagement with at least one of the rod extension and the adjuster. The intermediate piece may be in sliding engagement with both of the rod extension and the adjuster. In any case, the intermediate piece is configured to transfer an angular momentum or a torque from the adjuster to the rod extension.

According to a further example the intermediate piece is in rotational ratchet engagement or in a rotational frictional engagement with the piston rod. For this, the intermediate piece typically comprises at least one ratchet feature in ratchet engagement with a correspondingly shaped ratchet feature of the piston rod. When in a frictional engagement the intermediate piece comprises at least one or several friction faces that are in a dedicated and well-defined frictional engagement with a corresponding friction face of the piston rod. Typically, the ratchet feature or friction faces of the intermediate piece face radially outward and correspondingly shaped ratchet features or friction faces of the hollow piston rod face radially inward.

In one example the intermediate piece may be axially fixed to the piston rod. It may be in sliding engagement with the adjuster and it may be in sliding engagement with the rod extension. The intermediate piece may be in splined engagement with the rod extension. It may be in sliding and splined engagement with the adjuster while it is axially fixed to the piston rod.

The intermediate piece may be rotationally locked to the rod extension and may be further rotationally locked to the adjuster. The intermediate piece may be rotationally connected to the rod extension and may be further rotationally connected to the adjuster. A rotation of the adjuster relative to the piston rod leads to a respective rotation of the intermediate piece and further to a respective rotation of the rod extension relative to the piston rod. The ratchet engagement and/or the frictional engagement between the intermediate piece and the piston rod prevents an automated or self-acting rotation and hence a longitudinal displacement of at least one of the adjuster and the rod extension relative to the piston rod.

The intermediate piece may comprise a sleeve. The intermediate piece may comprise a hollow sleeve. A distal end of the intermediate piece may be in splined engagement with the rod extension, in particular with a proximally located rod section of the rod extension. A proximal end or a proximal section of the intermediate piece may be located inside a hollow portion of the adjuster. The adjuster may also comprise a hollow sleeve enclosing the proximal section of the intermediate piece. Mutually and radially overlapping portions of the rod extension and the intermediate piece may be in splined engagement. Mutually and radially overlapping portions of the intermediate piece and the adjuster may be also in splined engagement.

Typically, a distal end of the intermediate piece protruding distally from the distal end of the adjuster may be in ratchet engagement or frictional engagement with the piston rod.

In a further example the adjuster comprises a distal section and a proximal section. The distal section is operably engaged with the rod extension. It may be in splined engagement with the rod extension, e.g. by way of the intermediate piece. The proximal section of the adjuster is rotationally supported inside the driver. The proximal section or a proximal end of the adjuster may axially extend through the driver. In this way it is accessible from outside the driver and also from outside the housing of the injection device.

According to a further example the injection device comprises a button axially engaged or axially connected to the driver. A proximal end of the adjuster is arranged in a receptacle of a proximal end face of the button. The button and the driver may be integrally formed. Hence, the button may be a portion of the driver. Typically, the button forms a proximal end of the driver or is connected to a proximal end of the driver. The button is user operable. The button is displaceable in proximal direction for arming the injection device and/or for setting of a dose. The button is displaceable in distal direction for dispensing or expelling of the dose of the medicament.

The button is in sliding engagement with the injection device either directly or indirectly through the sliding engagement of the driver with the housing. By arranging the proximal end of the adjuster in a receptacle at a proximal end face of the button the proximal end of the adjuster is and remains accessible to a user of the injection device. The proximal end of the adjuster may be recessed compared to the proximal end face of the button. In this way the proximal end of the adjuster does not protrude from the proximal end face of the button. It does not influence or hinder the ordinary operation of the injection device, e.g. when a user uses his thumb to exert a distally directed driving motion onto the button or the driver.

According to another example the adjuster comprises a longitudinally extending sleeve section and a head. The head is radially widened compared to the sleeve section. The head is located at a proximal end of the sleeve section. The head further forms the proximal end of the adjuster. By means of the radially widened head, the adjuster can be axially fixed to the button and/or to the driver. The radially widened head of the adjuster may be axially confined inside the assembly of the driver and the button. In this way, the adjuster can be axially fixed to the assembly of the driver and the button. The sleeve section of the adjuster extends distally from the head. The sleeve section may comprise at least one spline feature that is rotationally locked to at least one of the intermediate piece and the rod extension.

According to a further example the head comprises a proximal end face that is located distally from the proximal end face of the button. In other words, the proximal end face of the head is recessed compared to the proximal end face of the button. It does not protrude from the button. Moreover, the proximal end face of the head may be provided with a longitudinal slot or slit. The longitudinal slot or slit may provide a screw slot configured to form a fit engagement with a screwdriver or screwing tool. A rotation of the adjuster relative to the piston rod may require use of a dedicated screwdriver or screwing tool. It is conceivable, that only authorized persons, such as caregivers will be equipped with the dedicated screwdriver or screwing tool. In this way and upon handing out the prefilled injection device to a patient, the caregiver or authorized person may adjust the dose size. The screw slot at the proximal end face of the adjuster further provides a kind of a safety feature thus preventing unauthorized manipulation of the adjuster and/or of the injection device.

According to a further example the injection device is equipped with a cartridge that is arranged inside the housing. The cartridge typically comprises a tubular shaped or cylindrical barrel. The barrel may comprise a vitreous barrel. A distal end of the barrel is sealed by a pierceable seal. The proximal end of the barrel is typically sealed by the bung that is displaceable in distal direction by means of the piston rod of the injection device.

In a further example, the adjuster comprises a sleeve section and the rod extension comprises a rod section. Here, the rod section and the sleeve section are located both inside a hollow cavity of the piston rod. Typically, the sleeve section comprises a hollow cavity in which the rod section of the rod extension is located. The rod section and the sleeve section may be rotationally locked to each other but may allow and support a longitudinal sliding displacement of the rod section relative to the sleeve section. It is also conceivable, that the rod section comprises a hollow cavity in which the sleeve section of the adjuster is located and rotationally locked with the rod section.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the true scope of the disclosure. Further, it is to be noted, that any reference numerals used in the appended claims are not to be construed as limiting the scope of the injection device.

BRIEF DESCRIPTION OF THE FIGURES

In the following, numerous examples of the container and of an injection device will be described in greater detail by making reference to the drawings, in which.

DETAILED DESCRIPTION

Figure 1:
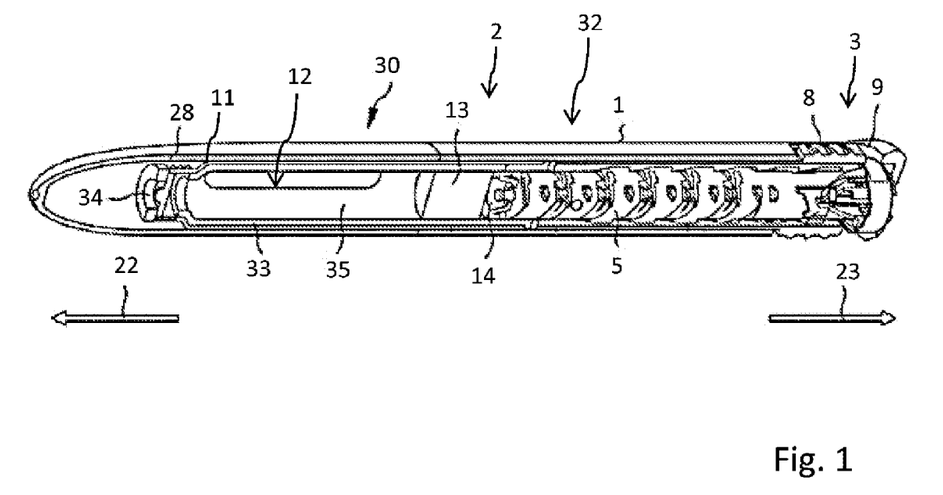
FIG. 1 shows an example of an injection device.

FIG. 1 shows a cut-away view of an injection device 30 configured as a pen injector and comprising a drive mechanism 32. The drive mechanism 32 is arranged in a body 1 or housing having a distal end 2 and a proximal end 3. A piston rod 5 is arranged along an axis 4 of the device. A screw thread 6 of the piston rod 5 is coupled to a drive feature of a piston rod nut 7 engaging the screw thread 6, in order to guide a helical movement of the piston rod 5 with respect to the piston rod nut 7. In further embodiments, the screw thread and the drive feature can be reversed such that the piston rod is provided with discrete drive features and the piston rod nut is provided with a helical screw thread. The piston rod nut 7 is rotationally locked to the body 1.

Figure 2:
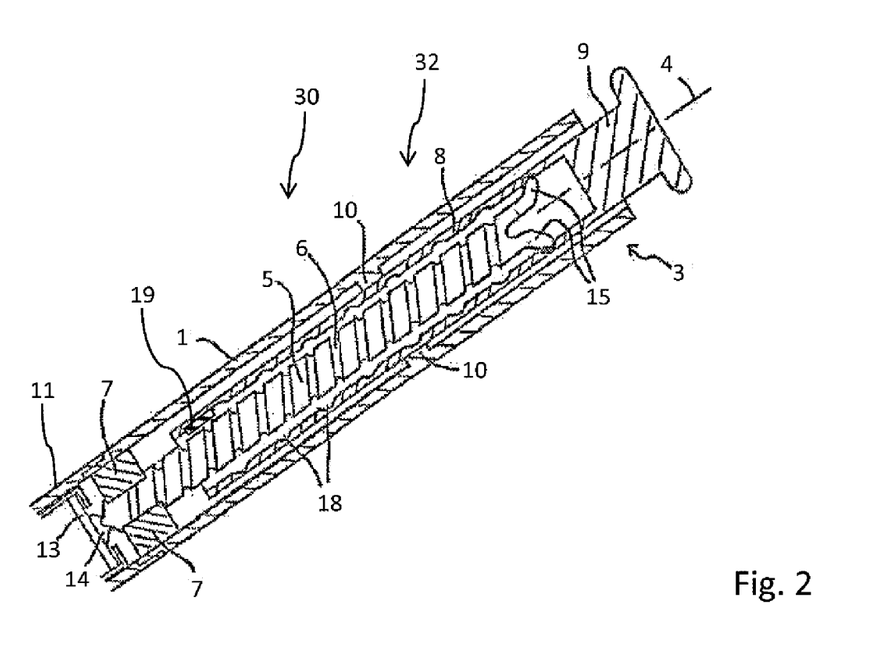
FIG. 2 shows a proximal portion of the injection device of FIG. 1 in a schematic representation.

The example of FIGS. 1 and 2 comprises a driver 8, which can be operated by the user by means of a button 9, which is arranged at the proximal end 3 and juts out of the body 1. The driver 8 is coupled or engaged with the piston rod 5. This is achieved by means of a screw thread 18 of the driver 8 and a flexible guide feature 15 of the piston rod 5. The driver 8 can especially be a drive sleeve of essentially cylindrical shape, the axis of the drive sleeve being arranged parallel to the axis 4 of the device. The piston rod 5 may be disposed to enter the driver 8.

A removable and attachable part 11 of the body 1 may be provided as a cartridge holder. When this part 11 is removed from the rest of the body 1, a cartridge 12 can be inserted. When the part 11 is attached to the body 1, the piston rod 5 is brought into contact with a piston 13, which is provided to expel a drug from the cartridge 12. A bearing 14 may be arranged between the piston rod 5 and the piston 13 in order to prevent any damage that might be caused by a relative movement between the piston rod 5 and the piston 13. The piston rod 5 functions as a lead screw to advance the piston 13 in the distal direction 22. The distal end of the cartridge 12 is provided with a pierceable seal 34 that is configured to be pierced by a double-tipped injection needle configured for attachment to a distal end of the attachable part 11 or cartridge holder. The vitreous barrel 33 is typically translucent so as to enable visual inspection of the medicament located inside the cartridge 12.

During a delivery operation, the piston rod 5 is helically moved in the distal direction 22 with respect to the body 1. The piston rod 5 is guided by the piston rod nut 7, which is engaged with the screw thread 6 of the piston rod 5. Stop features, described below, are provided in the screw thread 6 of the piston rod 5 to enable a dose setting operation, by which a fixed dose that is to be dispensed can be preset. For this purpose, the driver 8 is drawn in the proximal direction 23 relatively to the body 1 and to the piston rod 5. The driver 8 is coupled with the piston rod 5. In the embodiment shown in FIGS. 1 and 2, the coupling is achieved with the screw thread 18 of the driver 8 and the flexible guide feature 15 of the piston rod 5.

During the dose setting operation, the piston rod 5 must not be moved. Therefore, the engagement between the driver 8 and the piston rod 5 is temporarily released during the set operation. This may be achieved by a deformation of the flexible guide feature 15 to override the screw thread 18 of the driver 8. In spite of the engagement between the driver 8 and the piston rod 5, the driver 8 can therefore be moved without being rotated, while the piston rod 5 stays stationary with respect to the body. Overriding the engagement between the driver 8 and the piston rod 5 is facilitated by the flexible guide features 15, which can be bent towards the central axis 4. A rotation of the driver 8 with respect to the body 1 may be prevented by guide features 10, which may be protruding elements of the body 1 engaging an axial groove in the outer surface of the driver 8, for instance.

After the driver 8 has been moved a distance corresponding to the pitch of the screw thread 18 of the driver 8, the flexible guide feature 15 of the piston rod 5 re-engages the screw thread 18 of the driver 8, and the user can advance the piston rod 5 by pushing the driver 8 back in the distal direction 22. This method of operation by disengaging and reengaging the piston rod 5 with the driver 8 relies entirely on the piston rod 5 remaining substantially stationary during the setting operation. Should the piston rod rotate 5 or move axially during setting, then the driver 8 would very likely not correctly reengage with the piston rod 5 and thus cause dose inaccuracy. Therefore, the piston rod nut 7 guiding the helical movement of the piston rod 5 with respect to the body 1 is rotationally locked to the body 1 at least during the dispense operation and, furthermore, the piston rod 5 is provided with stop features interfering with the rotation of the piston rod 5 in such a manner that the rotation is inhibited in the positions of the piston rod 5 which are obtained after the drug delivery and before the setting of a new dose.

The rotation of the piston rod 5 is thus locked with respect to the piston rod nut 7, and the piston rod nut 7 is prevented from rotating relatively to the body 1. Therefore, when the driver 8 is drawn in the proximal direction 23, the relative linear motion between the driver 8 and the piston rod 5 causes the engagement of the driver 8 and the stationary piston rod 5 to be overridden and thus the engagement between the driver 8 and the piston rod 5 to be released. The stop features are therefore arranged at least on the distal sidewall of the screw thread 6 of the piston rod 5, while the screw thread 6 may be smooth, forming a helix, on its proximal sidewall. When the driver 8 is pushed in the distal direction, a guide means of the piston rod nut 7 engaging the screw thread 6 of the piston rod 5 stays in contact with the smooth proximal sidewall of the screw thread 6, thus enabling a smooth helical movement of the piston rod 5 sliding through the opening of the piston rod nut 7. Therefore, the stop features do not interfere with the relative motion of the piston rod 5 with respect to the piston rod nut 7 during the dispense operation.

The stop features may especially be provided by recesses of a helical groove forming the screw thread 6 of the piston rod 5. The recesses can have contact faces arranged transverse to the axis 4 and interrupting the smooth helix of the relevant sidewall of the groove forming the screw thread 6. The contact faces may especially be flat portions, essentially perpendicular to the axis 4 or at least having zero helix angle, but may comprise a rake angle in the radial direction. A drive feature of the piston rod nut 7 may be formed in such a manner that it enters the recesses and stops on the contact face. When the drive feature of the piston rod nut 7 comes into contact with one of the flat portions, the generally perpendicular orientation of the flat portion with respect to the axis 4 causes the guidance of the helical movement of the piston rod 5 with respect to the body 1 to be stopped. It may be favorable if the drive feature of the piston rod nut 7 that engages with the screw thread 6 of the piston rod 5 and is stopped in the recesses is made up of one or more individual drive features and is not formed by a completely continuous helix.

The stop features are arranged in such a fashion that, after a dose of the drug has been fully delivered and the device is ready for the next dose to be set, one of the stop features is in a position ready to stop the rotation of the piston rod 5 when the driver 8 is pulled in the proximal direction. The axial load exerted on the piston rod 5 is then compensated by the drive feature of the piston rod nut 7 engaging the relevant stop feature, particularly contacting the essentially flat portion of the relevant recess. This acts to lock the rotation of the piston rod 5 rather than rotate it, because the piston rod nut 7 is rotationally locked to the body 1 at least during the operations of setting and dispensing a dose. Essentially, the flat surfaces on the screw thread 6 are designed to prevent a back-driving of the piston rod 5 during a set operation. The motion of the piston rod 5 may thereby be restricted to the distal direction.

Figures 3, 4:
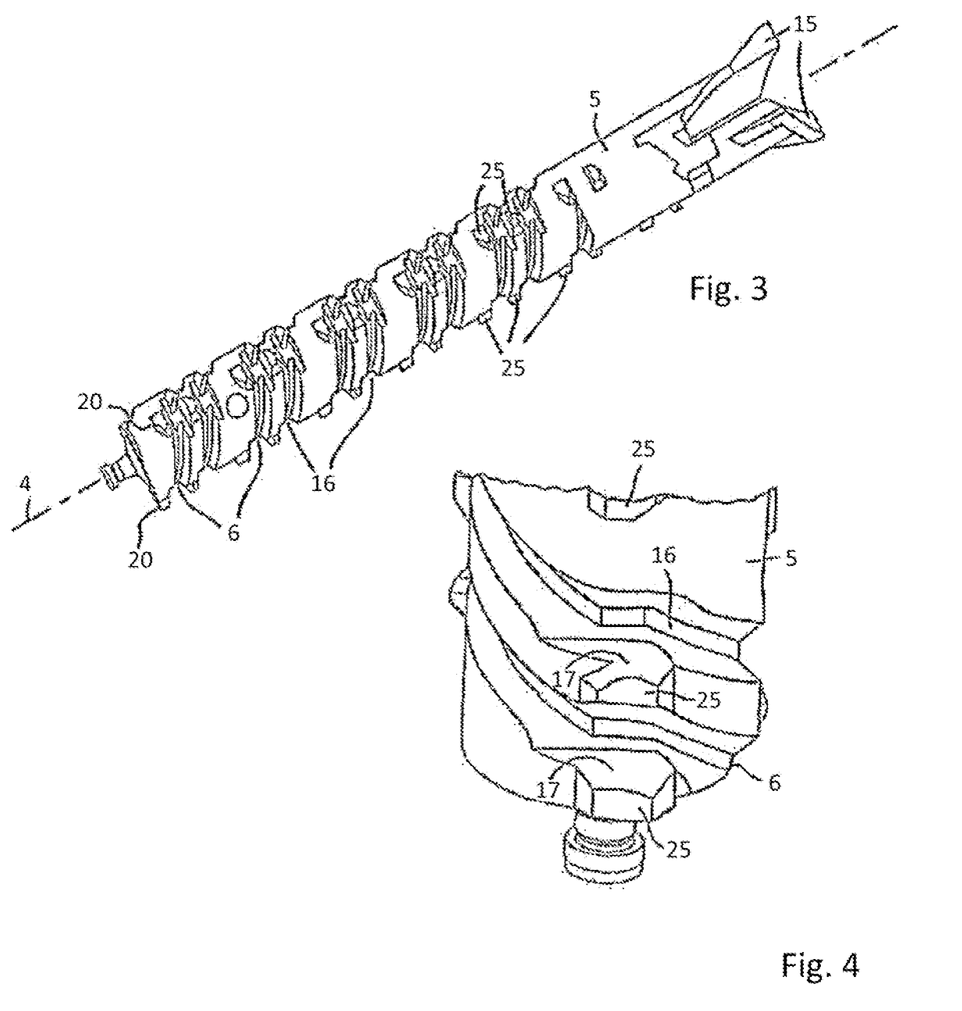
FIG. 3 illustrates a piston rod of the injection device.
FIG. 4 shows an enlarged view of the piston rod of FIG. 3.

FIG. 3 shows an enlarged perspective view of an embodiment of the piston rod 5. The piston rod 5 comprises a screw thread 6 and may comprise at least one further screw thread 16. If a further screw thread 16 is provided, the screw thread 6 and the further screw thread 16 have the same pitch and are intertwined. This means that the piston rod 5 has two co-axial helical features with separate entries at or near the distal end of the piston rod 5. The screw thread 18 of the driver 8 may also have two separate co-axial helical features, which are intertwined. The shape of the flexible guide feature 15 at the proximal end of the piston rod 5 is adapted to the screw thread 18 of the driver 8. The flexible guide feature 15 may especially comprise two co-axial helical male thread features provided to engage helical groves, which may form the screw thread 18 of the driver 8. If there are two co-axial helical features of the screw thread 18, there may be two separate parts of the flexible guide feature 15, each of the parts engaging one of the helical features. The flexible guide feature 15 can be deformed and thus disengaged from the screw thread 18 of the driver 8. This allows the coupling between the piston rod 5 and the driver 8 to be temporarily overridden when the driver 8 is pulled in the proximal direction 23.

The piston rod 5 is provided with spikes or spline features 25, which are arranged in a regular sequence. In the example of FIG. 3 there are three rows 20 of spline features 25 arranged parallel to the axis 4. The spline features 25 are located mainly in the region of the screw threads 6, 16 at the distal end of the piston rod 5. The rows 20 are spaced at 120° to each other around the circumference of the piston rod 5. The spacing may instead vary, or there may be another number of rows 20 of spline features 25. The spline features 25 are provided to interact with a stop feature 19 on an internal surface of the driver 8 which faces the piston rod 5.

The stop feature 19 may be a single protruding element, for instance, or may instead comprise two or more separate elements. The stop feature 19 helps to prevent the piston rod 5 from rotating when a dose is being set. Each row 20 of spline features 25 may comprise a series of positive protrusions that are positioned between the helical grooves of the screw threads 6, 16. As a result, there are gaps between the spline features 25. Every second gap between the spline features 25 is large enough to allow the corresponding stop feature 19 on the internal surface of the driver 8 to pass through during dispensing of a dose. The spline features 25 can also serve the further function of extending the line of contact between the piston rod 5 and the piston rod nut 7 at the transition between the helical thread sections and the stop features 17 of the screw threads 6, 16. This reduces the risk of deformation, particularly of the piston rod nut 7, in this region under high dispensing loads.

FIG. 4 shows an enlarged detailed view of the distal end of the piston rod 5. In this embodiment the piston rod 5 comprises a screw thread 6 and a further screw thread 16, which are intertwined and are provided with separate entries ("two-start" thread). The piston rod nut 7 engages the screw threads 6, 16 of the piston rod 5. The stop features 17 of the screw threads 6, 16 may be arranged in such a manner that their proximal surfaces extend continuously into the spline features 25 of at least one of the rows 20 of spline features 25, as can be seen from FIG. 4. The screw threads 6, 16 may be arranged at distances from one another that correspond to the different gaps between succeeding spline features 25. The spline features 25 may thus be arranged adjacent to the grooves of the screw threads 6, 16 and may especially be formed integrally with the stop features 17 of the screw threads 6, 16. Instead, only one screw thread 6 or more than two screw threads may be provided on the piston rod 5. In this case the spline features 25 are arranged along the rows 20 with the gaps between succeeding spline features 25 being alternatingly small and large, irrespective of the location of a helical groove of the thread.

The larger gaps are provided to permit the stop feature 19 of the driver 8 to pass through while a drug is being dispensed and the piston rod 5 is helically moved with respect to the driver 8. The smaller gaps are sufficiently small to prevent the stop feature 19 of the driver 8 to pass through when the driver 8 is pulled in the proximal direction to set a dose. In this case the spline features 25 slide along the stop feature 19 of the driver 8. This helps to prevent a rotation of the piston rod 5 with respect to the driver 8, which is rotationally locked with the body 1 and the piston rod nut 7. Consequently the piston rod 5 does not rotate with respect to the body 1 and the piston rod nut 7 either.

FIG. 2 shows the arrangement of the piston rod 5 and the driver 8, which is a drive sleeve surrounding the piston rod 5 in this embodiment. The distal end of the piston rod 5 juts out of the driver 8. The stop feature 19 is located on an inner sidewall of the driver 8 and may be a protruding element, for instance, or two separate protruding elements or a plurality of separate protruding elements. The stop feature 19 is preferably an integral part of the driver 8 and is formed in the inner sidewall. The axial dimension of each element of the stop feature 19 is sufficiently small to allow the element to pass between two neighboring spline features 25, if the gap between them is large. In a rest position that is occupied by the driver 8 with respect to the piston rod 5 after a dose has been dispensed, the stop feature 19 is at a position near two spline features 25 that are separated by a small gap.

If the next dose is to be set and the driver 8 is pulled in the proximal direction with respect to the body 1, the rotation of the piston rod 5 is inhibited by the stop feature 17 of the screw thread 6, which engages with the drive feature of the piston rod nut 7. Therefore the stop feature 19 of the driver 8 moves axially into a position adjacent to a spline feature 25, comes into contact with the spline feature 25, and slides along the spline feature 25 while the driver 8 is further moved relatively to the piston rod 5 in the proximal direction. The spline feature 25 prevents the stop feature 19 of the driver 8 from moving around the circumference of the piston rod 5 transversally to the axis 4 and thus prevents a rotation of the piston rod 5 with respect to the driver 8. When the stop feature 19 has passed the first spline feature 25, it slides in the same way axially along the following spline feature 25 of the same row 20, because the gap between the spline features 25 is small and does not allow the stop feature 19 to pass between the spline features 25. After the dose has been set, the stop feature 19 of the driver 8 is at a position from which it enters the large gap that is present between the neighboring spline features 25, when the driver 8 is pushed in the distal direction and a helical movement of the piston rod 5 is generated. An arrangement of a plurality of spline features 25 along the piston rod 5 is preferred because it always provides neighboring spline features 25 serving the purpose described above, irrespective of the position of the piston rod 5, which is advanced farther in the distal direction each time a dose is dispensed.

The design of the spline features 25 may deviate from the shape that is shown in the figures by way of example. The spline features 25 are arranged according to their purpose of either preventing a rotation of the piston rod 5 or enabling a helical movement of the piston rod 5, depending on the operation of the driver 8. The embodiment shown in the figures has the advantage that the arrangement of the spline features is adapted to the location of the helical grooves and the manufacturing of the device component is facilitated.

Figure 5:
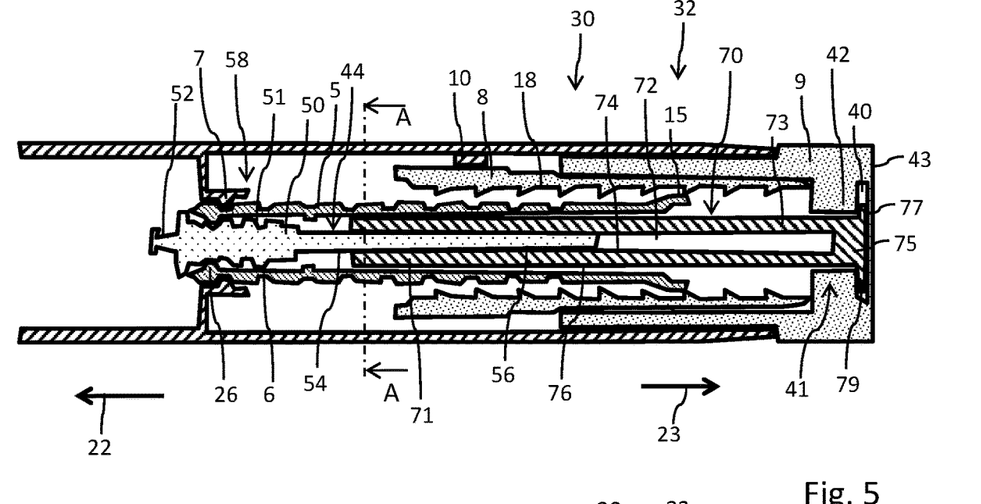
FIG. 5 shows a schematic cross-section through an example of the injection device.
Figure 7:
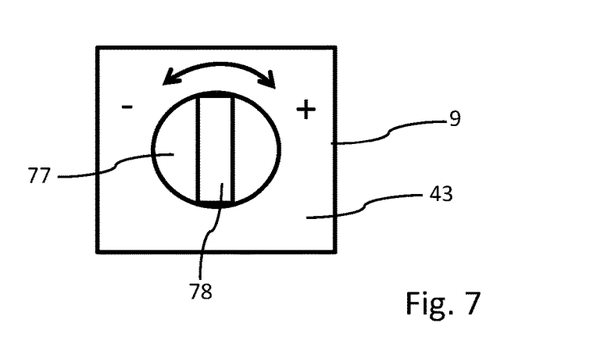

In FIGS. 5 and 7 an example of the injection device equipped with a dose size adjuster is illustrated. By way of example the drive mechanism 32 of the injection device 30 is based on the same working principle as described above in connection with FIGS. 1 to 4. The dose size adjuster as described herein may be also applied to other drive mechanisms of fixed dose devices.

As illustrated in FIG. 5 the piston rod 5 is hollow and comprises a hollow sleeve. The piston rod 5 comprises a hollow cavity 44 in which a rod extension 50 is arranged. The rod extension 50 and the piston rod 5 form or constitute a rod assembly 58. The rod extension 50 protrudes from a distal end of the piston rod 5. It is axially displaceable relative to the piston rod 5. In the present example the rod extension 50 and the piston rod 5 are threadedly engaged. For this the rod extension 50 comprises an outer thread 51 that is engaged with an inner thread 26 of the piston rod 5.

Due to the threaded engagement of the rod extension 50 and the piston rod 5 the rod assembly 58 can be of variable longitudinal length. The rod extension 50 comprises a stem 52 protruding in distal direction 22. The stem 52 forms or constitutes the distal end of the rod extension 50. The stem 52 rotationally supports the bearing 14, which is not particularly illustrated in FIGS. 5 and 6. The rod extension 50 is longitudinally displaceable relative to the piston rod 5 through a rotation relative to the piston rod 5. For this the rod extension 50 is operably engaged or is operably engageable with an adjuster 70. The adjuster 70 is arranged on or in the driver 8.

The adjuster 70 comprises a distal section 71 and a proximal section 73. The proximal section 73 is attached to the button 9 and/or to the driver 8. The button 9 and the driver 8 may be integrally formed. The proximal section 73 is provided with a radially widened head 75 that is arranged in a receptacle 40 of the button 9. The button 40 comprises a through opening 41 extending from the receptacle 40 in distal direction 22. The through opening 41 axially extends through a radially narrowed neck portion 42 of the button 9. In particular, the proximal end face of the neck portion 42 of the button 9 is in axial engagement with a distal face of the radially widened head 75 of the adjuster 70. The adjuster also comprises a sleeve section 76 extending in distal direction 22. The sleeve section 76 extends distally from the radially widened head 75. The outer diameter of the sleeve section 76 is smaller than the outer diameter of the head 75. The sleeve section 76 extends through the through opening 41. The radially widened head is axially confined in the receptacle 40 of the button 9. In this way the adjuster 70 is axially connected or axially engaged with the button 9.

The adjuster 70 is rotationally engaged or rotationally locked to the rod extension 50. As illustrated in FIG. 5 the sleeve section 76 of the adjuster 70 radially overlaps with a rod section 56 of the rod extension 50. The sleeve section 76 may form the distal section 71 of the adjuster 70, and the rod section 56 may overlap with the distal section 71. The rod section 56 forms a proximal portion or a proximal end of the rod extension 50. Both, the rod section 56 and the sleeve section 76 are located inside the hollow piston rod 5. The sleeve section 76 and the rod section 56 are in a splined engagement. The splined engagement forms a rotational interlock between the adjuster 70 and the rod extension 50 but allows for a longitudinal sliding displacement of the adjuster 70 relative to the rod extension 50. In this way the adjuster 70 is free to slide in proximal direction 23 relative to the rod extension 50 as the dose is set and when the button 9 is pulled in proximal direction 23.

Figure 8:
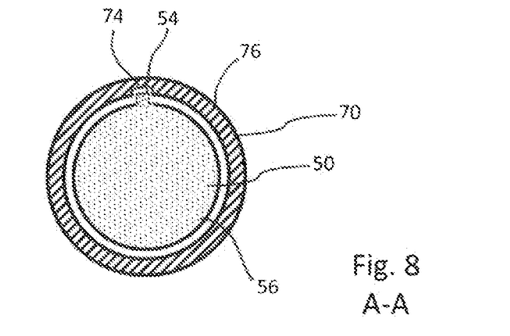

The splined engagement between the rod extension 50 and the adjuster 70 is formed by mutually corresponding spline features 54, 74 of the rod extension 50 and the adjuster 70, respectively. Here at least one of the spline features 54, 74 comprises a radial protrusion in sliding engagement with a correspondingly or complementary shaped radial recess of the other one of the spline feature 54 and the spline features 74. In the present example and as illustrated in FIG. 8 the rod extension 50 comprises a radially outwardly protruding spline feature 54 in rotational engagement with a correspondingly shaped spline feature 74 of the adjuster 70. The spline feature 54 comprises a radially outwardly extending protrusion on the outside surface of the rod extension 50, in particular at an outside facing portion of the rod section 56. The spline feature 74 is a radial recess provided on an inside facing sidewall section of the sleeve-shaped adjuster 70.

The spline feature 74 typically comprises an elongated groove on the inside surface of the sleeve section 76. As the adjuster 70 is subject to a longitudinal displacement relative to the body 1 and hence relative to the housing the mutually corresponding spline features 54, 74 remain engaged. This enables a torque transmission from the adjuster 70 to the rod extension 50 independent of the axial position of the adjuster 70, i.e. for each axial position of the adjuster 70. The size of the dose can be adjusted before setting of a dose or after setting of a dose, of course, before dispensing or expelling of the dose.

As illustrated in FIG. 5 the rod section 56 of the rod extension is located inside a cavity 72 of the adjuster 70 and is hence located inside a cavity 72 of the sleeve section 25. In an idle or initial configuration as illustrated in FIG. 5 the adjuster 70 can be rotated e.g. by means of a screwdriver or screwing tool to engage with a recess 78 formed as a screw slot at the proximal end face 77 of the adjuster 70. The proximal end face 77 of the adjuster 70 may be located distally from the proximal end face 43 of the button 9. In this way, the adjuster 70 can be rotated and actuated exclusively by means of a suitable screwing tool. This prevents unauthorized adjustment of a dose.

For adjusting of the dose the adjuster 70 is either rotated clockwise or counter-clockwise relative to the button 9. A clockwise or counter-clockwise rotation leads to a respective rotation of the rod extension 50 relative to the piston rod 5. In the present example as illustrated in FIG. 7 the adjuster 70 can be rotated clockwise in a first direction or first sense of rotation so as to increase the size of a dose. The adjuster 70 can be rotated in a second sense of rotation opposite to the first sense of rotation and hence counter-clockwise in order to reduce the size of a dose. When rotating the adjuster 70 in the second sense of rotation the respective screwing motion of the adjuster 70 is equally transferred to the rod extension 50. In accordance to the threaded engagement of the rod extension 50 with the piston rod, the rod extension 50 is subject to a proximally directed displacement relative to the piston rod 5. Here, the bearing 14 may lose contact with the proximal face of the bung or piston 13 of the cartridge 12.

When screwing or rotating the adjuster 70 in the first sense of rotation, e.g. clockwise, the rod extension 50 is displaced in distal direction 22 relative to the piston rod 5. Here, the entire drive mechanism 32 may be pretensed or prestressed and eventual mechanical play or geometric tolerances may be eliminated. It is intended that the adjuster 70 can only be rotated along the first sense of rotation to such an extent that a distally directed force exerted onto the bung or piston 13 is and remains below a breakaway force required for driving the piston 13 in distal direction 22.

In order to rotate the adjuster 70 relative to the piston rod 5 there may be provided at least one of a ratchet engagement and a frictional engagement between the adjuster 70 and the piston rod 5. The mechanical engagement between the adjuster 70 and the piston rod may comprise a unidirectional clutch or unidirectional ratchet engagement that is restricted to a unidirectional rotation of the adjuster 70 relative to the piston rod 5. The mechanical engagement between the adjuster 70 and the piston rod may be configured to support only a dose decrementing rotation of the adjuster 70 and may prevent a dose increasing adjustment motion of the adjuster 70.

In this way, the patient may be provided only with the possibility to decrease a size of a fixed dose but never to increase a size of a dose. This prevents a potential danger of overdosing.

With other examples and as illustrated here, the mechanical engagement between the adjuster 70 and the piston rod 5 is of bidirectional type. Here, the adjuster 70 can be rotated or moved relative to the piston rod 5 into opposite directions or senses of rotation. This allows to increase or to decrease a size of a fixed predefined dose.

In the example as illustrated in FIG. 5 the outside surface of the adjuster 70, in particular the outside surface of the sleeve section 76 may be in frictional engagement with an inside surface of the piston rod 5. In this way the adjuster 70 may be in frictional engagement with the piston rod 5. In order to rotate the adjuster 70 relative to the piston rod 5 a torque above a predefined adjusting torque must be applied to the adjuster 70. The adjusting torque is typically larger than a driving torque required for displacing the piston rod 5 in distal direction 22 during dispensing of the dose, i.e. a torque required to urge the piston 13 in distal direction 22 relative to the barrel 33 of the cartridge 12. In this way it can be provided that the rod extension 50 and the adjuster 70 remain rotationally locked to the piston rod 5 as the piston rod is subject to a rotation relative to the body 1 during a dose dispensing procedure.

Figure 6:
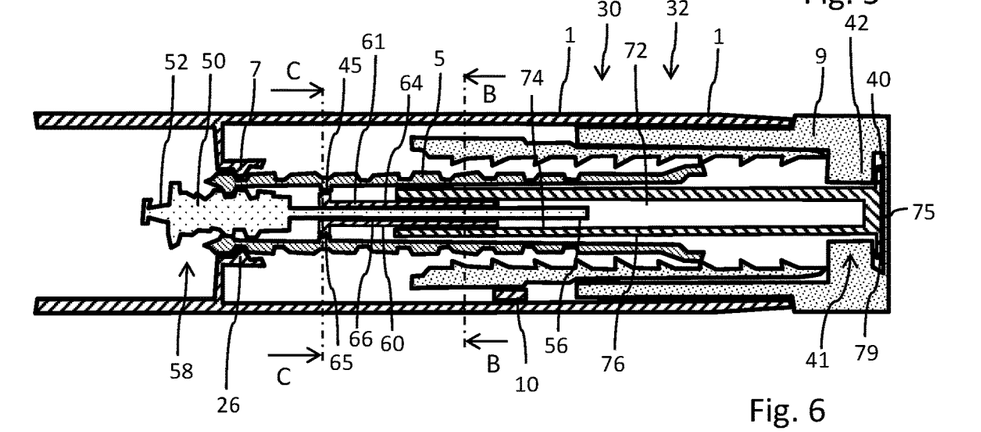
FIG. 6 shows a schematic cross-section through another example of the injection device, FIG. 7 schematically illustrates a proximal end face of the injection device, FIG. 8 schematically illustrates a cross-section along A-A in accordance to FIG. 5, FIG. 9 schematically illustrates a cross-section along B-B in accordance to FIG. 6 and FIG. 10 schematically illustrates a cross-section along C-C in accordance to FIG. 6.
Figure 9:
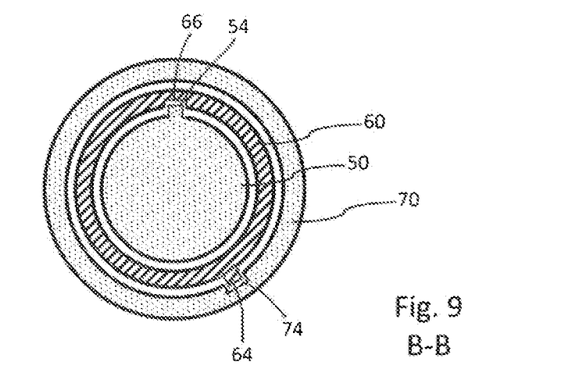
Figure 10:
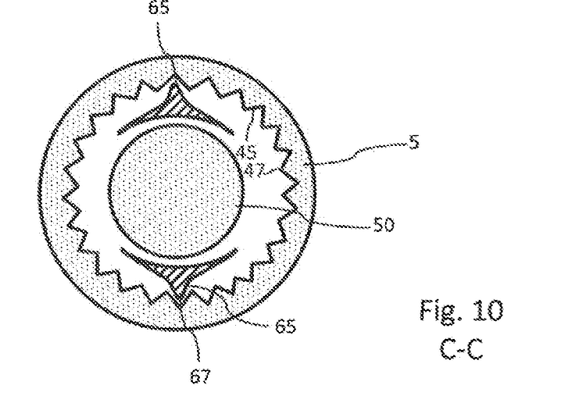

In FIGS. 6, 9 and 10 another example of the injection device 30 is illustrated. The example of FIG. 6 is further equipped with an intermediate piece 60. The intermediate piece 60 comprises a sleeve 61 that is radially sandwiched between the sleeve section 76 of the adjuster 70 and the rod section 56 of the rod extension 50. As illustrated in FIG. 9 the intermediate piece 60 is in splined engagement with both, the rod extension 50 and with the adjuster 70. For this the intermediate piece 60 comprises a spline feature 64 that is in engagement with the spline feature 74 of the adjuster 70. The intermediate piece 60 further comprises a further spline feature 66 that is in splined engagement with the spline feature 54 of the rod extension. In this way, the adjuster 70 is free to slide in longitudinal direction relative to the intermediate piece 60 while remaining rotationally locked to the intermediate piece 60.

In the same way the rod extension 50 is free to slide in longitudinal or axial direction relative to the intermediate piece 60 while it remains rotationally locked and rotationally connected to the intermediate piece 60. An adjusting torque applied from a user to the adjuster 70 is transferable by the intermediate piece 60 to the rod extension 50 thus leading to a variation of the total elongation of the rod assembly 58.

As it is apparent from FIG. 6 and FIG. 10 the intermediate piece 60 is in permanent ratchet engagement with the piston rod 5. For this the piston rod 5 comprises a ratchet feature 45 at an inside sidewall. The ratchet feature 45 comprises a toothed ring extending along the inner circumference of the hollow piston rod 5. The toothed ring comprises numerous radially inwardly protruding teeth 47. The correspondingly shaped ratchet feature 65 of the intermediate piece 60 comprises at least one radially outwardly extending tooth 67 that is in ratchet engagement with consecutive teeth 47 of the ratchet feature 45.

As illustrated in FIG. 10 the intermediate piece 60 comprises two oppositely located ratchet features 65. The ratchet features 65 may be located on one or several flexible arms that are configured to bend or to deflect radially inwardly as the intermediate piece 60 is rotated relative to the piston rod 5. There may be provided two or even more oppositely or equidistantly arranged arms with ratchet features 65. In this way a holding torque can be split among the various teeth 67 of the ratchet features 65. The ratchet engagement of the intermediate piece 60 with the piston rod 5 defines a holding torque and prevents a self-actuated or automated rotation of the rod extension 50 relative to the piston rod 5 during a dose dispensing procedure.

For adjusting of the size of the fixed dose an adjusting torque must be applied to the adjuster 70 and hence to the intermediate piece 60, wherein the adjusting torque is larger than the holding torque. Accordingly, the ratchet features 65 will be subject to a radially inwardly directed motion that allows and supports a well-defined stepwise rotation of the intermediate piece 60 and hence of the rod extension 50 relative to the piston rod 5. For setting of a dose the piston rod 5 is hindered to rotate due to the above described interaction of the stop features 17, 19 as well as due to the threaded engagement with the driver 8.

LIST OF REFERENCE NUMBERS 1 body
2 distal end
3 proximal end
4 axis
5 piston rod
6 screw thread
7 screw nut
8 driver
9 button
10 guide feature
11 attachable part
12 cartridge
13 piston
14 bearing
15 flexible guide feature
16 screw thread
17 stop feature
18 screw thread
19 stop feature
20 row
22 distal direction
23 proximal direction
25 spline feature
26 thread
30 injection device
32 drive mechanism
33 barrel
34 pierceable seal
35 medicament
40 receptacle
41 through opening
42 neck portion
43 end face
44 cavity
45 ratchet feature
47 tooth
50 rod extension
51 thread
52 stem
54 spline feature
56 rod section
58 rod assembly
60 intermediate piece
61 sleeve
64 spline feature
65 ratchet feature
66 spline feature
67 tooth
70 adjuster
71 distal section
72 cavity
73 proximal section
74 spline feature
75 head
76 sleeve section
77 end face
78 recess
79 proximal end

The invention claimed is:

1. An injection device configured to expel a dose of a medicament, the injection device comprising:
an elongated housing extending in a longitudinal direction,
a piston rod movable relative to the elongated housing in a longitudinal distal direction to exert a dispensing pressure onto a bung of a cartridge at least partially filled with an injectable medicament,
a rod extension movably arranged on or in a distal end of the piston rod,
a driver operably engaged with the piston rod and movable relative to the elongated housing in a longitudinal proximal direction for setting the dose and movable relative to the elongated housing in the longitudinal distal direction for dispensing the dose, and
an adjuster arranged on or in the driver and operably engaged with the rod extension to move the rod extension in the longitudinal direction relative to the piston rod, wherein the rod extension is threadedly engaged with the distal end of the piston rod.

2. The injection device according to claim 1, wherein the driver is rotationally locked to the elongated housing.

3. The injection device according to claim 1, wherein the driver is threadedly engaged with the piston rod.

4. The injection device according to claim 1, wherein the piston rod comprises at least one flexible guide feature that is threadedly engaged with a screw thread of the driver.

5. The injection device according to claim 1, wherein the adjuster is axially engaged with the driver.

6. The injection device according to claim 1, wherein the adjuster is in a longitudinal sliding engagement with the rod extension.

7. The injection device according to claim 1, wherein the adjuster is rotationally locked to the rod extension.

8. The injection device according to claim 1, wherein the adjuster is rotatable relative to the piston rod when an adjusting torque above a predefined holding torque is applied to the adjuster.

9. The injection device according to claim 8, wherein the predefined holding torque is larger than a driving torque required for displacing the piston rod in distal direction during dispensing of the dose.

10. The injection device according to claim 8, further comprising at least one of a frictional engagement and a ratchet engagement between the adjuster and the piston rod, wherein the at least one of the frictional engagement and the ratchet engagement defines the predefined holding torque.

11. The injection device according to claim 1, further comprising an intermediate piece arranged between the rod extension and the adjuster, wherein the intermediate piece is rotationally locked to the rod extension and to the adjuster.

12. The injection device according to claim 11, wherein the intermediate piece is in longitudinal sliding engagement with at least one of the rod extension and the adjuster, and wherein the intermediate piece is in rotational ratchet engagement with the piston rod.

13. The injection device according to claim 1, wherein the adjuster comprises a distal section and a proximal section, wherein the distal section of the adjuster is operably engaged with the rod extension and wherein the proximal section of the adjuster is rotationally supported inside the driver.

14. The injection device according to claim 1, further comprising a button axially engaged with the driver, wherein a proximal end of the adjuster is arranged in a receptacle of a proximal end face of the button.

15. The injection device according to claim 14, wherein the adjuster comprises a longitudinally extending sleeve section and a head, wherein the head is radially widened compared to the sleeve section, wherein the head is located at a proximal end of the sleeve section and wherein the head forms the proximal end of the adjuster.

16. The injection device according to claim 15, wherein the head comprises a proximal end face that is located distally from the proximal end face of the button.

17. The injection device according to claim 1, further comprising the cartridge arranged inside the elongated housing.

18. The injection device according to claim 1, wherein the piston rod is threadedly engaged with the elongated housing.

19. The injection device according to claim 1, wherein the adjuster comprises a sleeve section, wherein the rod extension comprises a rod section, and wherein the rod section and the sleeve section are located inside a hollow cavity of the piston rod.

20. An injection device configured to expel a dose of a medicament, the injection device comprising:
   an elongated housing extending in a longitudinal direction,
   a piston rod movable relative to the elongated housing in a longitudinal distal direction to exert a dispensing pressure onto a bung of a cartridge at least partially filled with an injectable medicament,
   a rod extension movably arranged on or in a distal end of the piston rod,
   a driver operably engaged with the piston rod and movable relative to the elongated housing in a longitudinal proximal direction for setting the dose and movable relative to the elongated housing in the longitudinal distal direction for dispensing the dose, and
   an adjuster arranged on or in the driver and operably engaged with the rod extension to move the rod extension in the longitudinal direction relative to the piston rod, wherein the adjuster is rotatable relative to the piston rod when an adjusting torque above a predefined holding torque is applied to the adjuster.

21. An injection device configured to expel a dose of a medicament, the injection device comprising:
   an elongated housing extending in a longitudinal direction,
   a piston rod movable relative to the elongated housing in a longitudinal distal direction to exert a dispensing pressure onto a bung of a cartridge at least partially filled with an injectable medicament,
   a rod extension movably arranged on or in a distal end of the piston rod,
   a driver operably engaged with the piston rod and movable relative to the elongated housing in a longitudinal proximal direction for setting the dose and movable relative to the elongated housing in the longitudinal distal direction for dispensing the dose, and
   an adjuster arranged on or in the driver and operably engaged with the rod extension to move the rod extension in the longitudinal direction relative to the piston rod and wherein the piston rod comprises at least one flexible guide feature that is threadedly engaged with a screw thread of the driver.

* * * * *